United States Patent [19]
Smith et al.

[11] Patent Number: 5,977,426
[45] Date of Patent: *Nov. 2, 1999

[54] CRYSTALLIZATION OF 2,6-DIMETHYLNAPHTHALENE

[75] Inventors: Thomas G. Smith; John M. Weis; Yenamandra Viswanath, all of Naperville, Ill.

[73] Assignee: BP Amoco Corporation, Chicago, Ill.

[*] Notice: This patent issued on a continued prosecution application filed under 37 CFR 1.53(d), and is subject to the twenty year patent term provisions of 35 U.S.C. 154(a)(2).

[21] Appl. No.: 08/957,871

[22] Filed: Oct. 20, 1997

Related U.S. Application Data

[63] Continuation of application No. 08/452,876, May 30, 1995, abandoned, which is a continuation of application No. 08/180,104, Dec. 29, 1993, Pat. No. 5,510,563.

[51] Int. Cl.⁶ ..................................................... C07C 7/14
[52] U.S. Cl. ........................... 585/812; 585/804; 585/805; 585/452; 585/467
[58] Field of Search ..................................... 585/812, 804, 585/805, 452, 467

[56] References Cited

U.S. PATENT DOCUMENTS

| | | | |
|---|---|---|---|
| 3,153,676 | 10/1964 | Allen et al. | 585/812 |
| 3,202,726 | 8/1965 | Malmberg et al. | 585/812 |
| 3,485,885 | 12/1969 | Peterkin et al. | 585/812 |
| 3,541,175 | 11/1970 | Hedge | 585/252 |
| 3,590,091 | 6/1971 | Skarada et al. | 585/812 |
| 3,594,436 | 7/1971 | Hedge et al. | 585/240 |
| 3,775,496 | 11/1973 | Thompson | 585/320 |
| 3,806,552 | 4/1974 | Oka et al. | 585/478 |
| 4,791,235 | 12/1988 | Maki et al. | 585/806 |
| 5,198,594 | 3/1993 | Lillwitz et al. | 585/467 |

FOREIGN PATENT DOCUMENTS 1354479  1/1974  United Kingdom .

*Primary Examiner*—Elizabeth D Wood
*Attorney, Agent, or Firm*—Thomas E. Nemo; Scott P. McDonald; Stephen L. Hensley

[57] ABSTRACT

A method for recovering crystalline 2,6-dimethylnaphthalene comprising crystallizing in a scraped-wall crystallizer apparatus at crystallization temperature T, a mixture of low melting components, LM, having melting points of 70° F. and below, and high melting components (HM), including 2,6-dimethylnaphthalene, having melting points above 70° F, such that:

$$\frac{HM}{LM} < 0.03(T - 50) + A,$$

where HM is the total weight percent of high melting components, including 2,6-dimethylnaphthalene, in the mixture, and LM is the total weight percent of low melting components in the mixture, and where T is the temperature of the crystallization in degrees Fahrenheit, and where A is at least 1.0.

9 Claims, 2 Drawing Sheets

CRYSTALLIZATION OF 2,6-DIMETHYLNAPHTHALENE

This is a continuation of application Ser. No. 08/452,876, filed May 30, 1995, now abandoned, which is a continuation of application Ser. No. 08/180,104 filed on Dec. 29, 1993, now U.S. Pat. No. 5,570,563.

FIELD OF THE INVENTION

This invention relates to an improved method for recovering 2,6-dimethylnaphthalene by crystallization from a mixture containing 2,6-dimethylnaphthalene and organic components formed during the preparation or isolation of 2,6-dimethylnaphthalene. More particularly, this invention relates to a method for recovering 2,6-dimethylnaphthalene from a mixture containing dimethylnaphthalenes, wherein the composition of the mixture is adjusted to provide for efficient crystallization of the 2,6-dimethylnaphthalene.

BACKGROUND OF THE INVENTION 2,6-Dimethylnaphthalene is a preferred feedstock for preparing 2,6-naphthalenedicarboxylic acid. 2,6-Naphthalenedicarboxylic acid is a useful monomer for the preparation of high performance polymeric materials. For example, 2,6-naphthalenedicarboxylic acid, or its methyl ester, can be reacted with ethylene glycol to prepare poly(ethylene-2,6-naphthalate) (PEN). Fibers and film manufactured from PEN have improved strength and superior thermal properties relative to other polyester materials. Films made from PEN demonstrate, for example, superior resistance to gas diffusion and particularly to the diffusion of carbon dioxide, oxygen and water vapor. Because of its exceptional properties, PEN is especially suitable for applications such as food and beverage containers, particularly for so-called "hot-fill" food and beverage containers, tire cord, magnetic recording tape and electronic components.

Although 2,6-naphthalenedicarboxylic acid can be prepared by a number of processes, perhaps the most preferred because of cost and efficiency, is the liquid phase oxidation of 2,6-dimethylnaphthalene. A suitable method for oxidizing 2,6-dimethylnaphthalene to 2,6-naphthalenedicarboxylic acid is described, for example, in U.S. Pat. No. 5,183,933 to Harper et al. Although feedstocks other than 2,6-dimethylnaphthalene, for example 2,6-diethylnaphthalene or 2,6-diisopropylnaphthalene, can be oxidized to 2,6-naphthalenedicarboxylic acid, 2,6-dimethylnaphthalene is preferred because it is lower in molecular weight compared to 2,6-diethyl- or 2,6-diisopropylnaphthalene and, therefore, less 2,6-dimethylnaphthalene (by weight) is required to prepare a specified weight amount of 2,6-naphthalenedicarboxylic acid.

While 2,6-dimethylnaphthalene is present in certain refinery streams, for large scale use it is preferable to manufacture 2,6-dimethylnaphthalene starting with simple, readily available and inexpensive starting materials. One such process for manufacturing 2,6-dimethylnaphthalene is disclosed in Lillwitz et al., U.S. Pat. No. 5,198,594. The process for preparing 2,6-dimethylnaphthalene disclosed therein is called the "Alkenylation Process," which comprises reacting o-xylene with butadiene in the presence of a zero-valent alkali metal to form orthotolylpentene (OTP). The alkali metal-promoted reaction of an alkylaromatic with a conjugated diene such as butadiene to form an olefinically substituted aromatic is referred to as an alkenylation reaction. The OTP is subsequently cyclized to form 1,5-dimethyltetralin (1,5-DMT), the 1,5-DMT is dehydrogenated to 1,5-dimethylnaphthalene (1,5-DMN) and the 1,5-DMN is isomerized to the desired 2,6-dimethylnaphthalene (2,6-DMN). The overall process is summarized in equations (1) through (4) below.

In the alkenylation process for preparing 2,6-dimethylnaphthalene, the isomerization of 1,5-dimethylnaphthalene typically produces not only the desired 2,6-dimethylnaphthalene, but also a mixture of other hydrocarbon components such as 1,6- and 1,7-dimethylnaphthalenes and 1- and 2-monomethylnaphthalenes and various trimethylnaphthalenes. Additionally, other processes for preparing 2,6-dimethylnaphthalene and methods for isolating 2,6-dimethylnaphthalene from refinery streams generally require recovering the 2,6-dimethylnaphthalene from a mixture containing other hydrocarbons. In order to have a cost-effective process for preparing 2,6-dimethylnaphthalene, it is necessary to efficiently isolate the 2,6-dimethyl-naphthalene from the mixture of hydrocarbons produced by the isomerization reaction, the hydrocarbon mixtures produced by other processes for preparing 2,6-dimethylnaphthalene, or mixtures produced during the processes for isolating 2,6-dimethylnaphthalene from refinery streams. The art, therefore, needs a simple and cost effective method for recovering valuable 2,6-dimethylnaphthalene from a mixture containing 2,6-dimethylnaphthalene and other hydrocarbon components. The present invention provides such a method.

Methods for isolating 2,6-dimethylnaphthalene from mixtures of hydrocarbons are known. For example, U.S. Pat. No. 3,806,552 to Oka et al., discloses that the separation of 2,6-dimethylnaphthalene from the isomerization reaction product can be easily carried out by cooling the isomerization reaction product to a proper temperature and separating the precipitated crystals, or by adding a suitable solvent to the isomerization reaction product, cooling the solution and separating the precipitated crystals. A number of suitable solvents are disclosed therein. U.S. Pat. No. 3,775,496 to Thompson et al., discloses that selective crystallization has been used to separate DMN (dimethylnaphthalenes) from each other, citing U.S. Pat. Nos. 3,485,885; 3,541,175; 3,590,091 and 3,594,436. U.S. Pat. No. 3,541,175 discloses a process for isolating 2,6-dimethylnaphthalene, and it discloses that crystallization may be carried out in a scraped cooling crystallizer. British Patent 1,345,479 discloses that 2,6-dimethyl-naphthalene can be isolated by crystallization. As an example, 2,6-DMN is crystallized from a mixture containing 35.3 mol.% to 2,6-DMN, 36.8% 1,6-DMN, 8% 1,5-DMN, 7.7% 1,7-DMN and 4.2% low-boiling point and high-boiling point by-products.

SUMMARY OF THE INVENTION

A method for preparing crystalline 2,6-dimethylnaphthalene comprising crystallizing in a scraped-wall crystallizer apparatus at crystallization temperature T, a mixture of low melting components, LM, having melting points of 70° F. and below, and high melting components, HM, including 2,6-dimethylnaphthalene, having melting points above 70° F., such that:

$$\frac{HM}{LM} < 0.03\,(T-50) + A, \quad (5)$$

where HM is the total weight percent of high melting components, including 2,6-dimethylnaphthalene, in the mixture, and LM is the total weight percent of low melting components in the mixture, and where T is the temperature of the crystallization in degrees Fahrenheit, and where A is a value no more than about 1.0.

This invention is also a method for preparing crystalline 2,6-dimethylnaphthalene comprising maintaining, at a temperature sufficient to cause the crystallization of 2,6-dimethylnaphthalene, a mixture comprising 2,6-dimethylnaphthalene, at least one of 1,6- or 1,7-dimethylnaphthalene, and at least about 5 weight percent light-boiling components produced during the preparation or isolation of 2,6-dimethyl-naphthalene.

DETAILED DESCRIPTION OF THE INVENTION

We discovered that 2,6-dimethylnaphthalene can be effectively crystallized in a scraped-wall crystallization apparatus provided the weight ratio of high melting components (HM), which includes 2,6-dimethylnaphthalene, to low melting components (LM) in the mixture being crystallized is as follows:

$$\frac{HM}{LM} < 0.03\,(T-50) + A, \quad (5)$$

where T is the temperature, in degrees Fahrenheit, used for the crystallization and A is no more than about 1.0. We have determined that when the ratio of HM/LM is outside of this range, the scraped-wall crystallizer cannot effectively crystallize the 2,6-dimethylnaphthalene. Specifically, the mixture being crystallized forms a solid mass that clings to the scraping device in the crystallizer and the crystallizer becomes inoperable. In contrast, when the crystallization operation is conducted within the operable range of equation (5), the product exiting the scraped-wall crystallizer is in the form of a slurry of crystalline 2,6-dimethylnaphthalene in the crystallization mother liquor. Additionally, we have determined that the weight ratio of high melting components to low melting components in the mixture subjected to crystallization can be adjusted to the desired composition by utilizing the light boiling components (lights) that are produced during the preparation or isolation of 2,6-dimethylnaphthalene. These lights, for example, can comprise the mixture of components having a lower boiling point than the dimethyl-naphthalenes, and which components are produced during the process steps for preparing 2,6-dimethylnaphthalene using the alkenylation process. Instead of removing these lights, we have determined that the amount of lights present during the crystallization of the 2,6-dimethylnaphthalene can be adjusted by, for example, fractionation prior to crystallization. The composition produced thereby provides for the efficient crystallization of 2,6-dimethylnaphthalene, particularly when a scraped-wall crystallizer apparatus is used to conduct the crystallization. In equation (5) above, T is preferably in the range of 50 to about 150° F., more preferably 60 to about 140° F.

The method of this invention is advantageously used to isolate 2,6-dimethylnaphthalene produced by the alkenylation process. As described hereinabove and summarized in Equations (1) to (4) hereinabove, the alkenylation process comprises four basic chemical reaction steps. In the first step, the alkenylation reaction, o-xylene is reacted with butadiene to produce an orthotolylpentene (OTP). The OTP formed is actually a mixture of 5-OTP-1 and cis- and trans-5-OTP-2. A suitable method for preparing orthotolylpentene is disclosed in Lillwitz et al., U.S. Pat. No. 5,198,594; other methods are disclosed in U.S. Pat. Nos. 3,766,288 and 3,953,535 to Shima et al. The specification of these three patents are hereby incorporated by reference. In this alkenylation reaction, o-xylene in the liquid phase is reacted with 1,3-butadiene in the presence of a catalytic amount of an alkali metal. Typically, an excess molar amount of o-xylene is used in order to reduce the amount of high molecular weight by-products that are formed resulting from the reaction of more than one molecule of butadiene per molecule of o-xylene. For example, 1,3-butadiene can be reacted with about 1.1 to about 20 moles of o-xylene per mole of 1,3-butadiene, in the liquid phase, at a temperature of about 200° F. to about 320° F. and at a pressure of about 1 atmosphere to about 3 atmospheres to form a product mixture comprising orthotolylpentene. The reaction is suitably catalyzed by an alkali metal such as potassium or a mixture of potassium and sodium, preferably NaK. The amount of alkali metal is about 1 to about 10,000 parts by weight per million parts by weight of o-xylene. After the alkenylation reaction, the reactive alkali metal can be quenched with, for example, water or an alcohol, and the excess o-xylene is removed to produce a concentrate containing the desired orthotolylpentene. The concentrate can be fractionated to remove materials having boiling points higher and/or lower than orthotolylpentene to form a purified form of orthotolylpentene. However, the concentrate containing components having a lower and higher boiling point than orthotolylpentene can also be used directly in the cyclization step.

In the cyclization step of the alkenylation process, the orthotolylpentene is cyclized using a catalyst to form 1,5-dimethyltetralin. Methods for cyclizing orthotolylpentene, as well as suitable catalysts, are disclosed in U.S. Pat. Nos. 5,034,561; 5,030,781 and 5,073,670, to Sikkenga et al., the specifications of which are hereby incorporated by reference. Other processes for cyclizing orthotolylpentene to dimethyltetralin are disclosed, for example, in U.S. Pat. Nos. 3,775,498; 3,775,496 and 3,840,609, the specifications of which are hereby incorporated by reference. The cyclization reaction can be conducted using either a gaseous or liquid phase reaction. A preferred method for cyclizing orthotolylpentene to 1,5-dimethyltetralin uses an acidic molecular sieve catalyst such as a low-acidity, ultrastable crystalline aluminosilicate zeolite Y in the hydrogen form having a silica-to-alumina bulk molar ratio of at least about 12, a unit cell size no greater than 24.3 Angstroms, a sodium content of no more than about 0.4 weight percent sodium or, in terms of sodium oxide, a sodium oxide-to-alumina bulk molar ratio in the range of about 0.001:1 to about 1:1. The cyclization reaction comprises maintaining the orthotolylpentene in the liquid phase at a temperature of about 120° C. to about 350° C., at a pressure, for example, of about 0.05 to about 0.5 atmospheres, to form a reaction mixture comprising the 1,5-dimethyltetralin. The weight ratio of orthotolylpentene to the molecular sieve cyclization catalyst is suitably about 1000:1 to about 10:1. The mixture produced by the cyclization reaction can be used directly for the next reaction in the alkenylation process; alternatively, the reaction product mixture from the cyclization reaction can be fractionated to remove light and/or heavy components and thereby prepare a concentrate of 1,5-dimethyltetralin.

In the next step of the alkenylation process, the mixture produced by the cyclization reaction, or the concentrate prepared by fractionating the product from the cyclization reaction, is dehydrogenated to prepare 1,5-dimethylnaphthalene. This dehydrogenation can be accomplished using either a gas phase reaction or a liquid phase reaction. Suitable methods and catalysts for conducting such a dehydrogenation reaction are disclosed in U.S. Pat. Nos. 5,118,892; 5,189,234; 3,775,498 and 3,781,375, the specifications of which are hereby incorporated by reference. A preferred method comprises contacting the 1,5-dimethyltetralin in the gas phase with a suitable dehydrogenation catalyst such as a catalyst comprising alumina, about 0.05 to about 5.0 weight percent platinum or palladium, no more than about 0.14 weight percent halide, and about 0.10 to about 2.0 weight percent alkali metal, all weight percents based on the weight of the catalyst, at a temperature of about 600 to about 900° F., a pressure of about 0.01 atmosphere to about 25 atmospheres, and at a weight hourly space velocity of about 0.1 $hr^{-1}$ to about 20 $hr^{-1}$. The mixture produced by the dehydrogenation reaction can be used directly in the isomerization reaction; alternatively, it can be fractionated to remove lower boiling components and/or higher boiling components, for example, those formed during the dehydrogenation reaction. The product from the dehydrogenation reaction, either in fractionated or unfractionated form, is isomerized over a suitable catalyst to form a mixture of dimethylnaphthalenes, including the desired 2,6-dimethylnaphthalene. Suitable methods for isomerizing 1,5-dimethylnaphthalene are disclosed, for example, in U.S. Pat. Nos. 4,962,260; 4,950,825; 3,775,498; 3,781,375; 3,855,328 and 3,957,896, the specifications of which are hereby incorporated by reference. A suitable method for isomerizing 1,5-dimethylnaphthalene comprises contacting 1,5-dimethylnaphthalene in the liquid phase at a temperature in the range of about 200° C. to about 420° C. with an acidic isomerization catalyst. For example, the catalyst can comprise either an acidic ultrastable crystalline y-zeolite having a silica-to-alumina molar ratio of from about 4:1 to about 10:1, having pore windows provided by twelve-membered rings containing oxygen and a unit cell size of from about 24.2 to about 24.7 angstroms, or beta-zeolite.

The product from this isomerization reaction contains 2,6-dimethyl-naphthalene. Preferably, the product from the isomerization contains at least about 20, more preferably at least about 35 weight percent 2,6-dimethylnaphthalene. In addition, depending on the conditions used for the isomerization, and whether or not prior fractionation steps were used to remove high boiling and low boiling components from the product mixtures produced during the preceding alkenylation, cyclization, dehydrogenation and isomerization steps, the product mixture produced by the isomerization reaction can contain in addition to the dimethyl-naphthalenes, about 1 to about 20 weight percent of light, low boiling components (lights), about 0.5 to about 5 weight percent of various trimethylnaphthalenes and about 0.5 to about 5 weight percent of the heavy, high boiling components (heavies). By light, low boiling, we mean that the boiling point of the component is lower than the boiling point of 2-methylnaphthalene. Thus, the light, low boiling components (lights) have a boiling point lower than about 500° F., preferably lower than about 470° F, at atmospheric pressure. By heavy, high boiling, we mean having a boiling point greater than the boiling point of any of the dimethylnaphthalenes, more preferably greater than the boiling point of the trimethylnaphthalenes. Thus, the heavy, high boiling components (heavies) have a boiling point greater than about 520° F. at atmospheric pressure. In addition to the above, the product produced by the isomerization reaction can contain various other dimethylnaphthalenes in addition to the desired 2,6-dimethylnaphthalene. Such dimethylnaphthalenes include one or more of 1,6- and 1,7-dimethylnaphthalene, preferably at least 1,6-dimethylnaphthalene, and typically about 40 to about 80 weight percent of such other dimethylnaphthalenes.

As described hereinabove, instead of removing the light, low-boiling components prior to crystallizing the 2,6-dimethylnaphthalene, they can be included, in variable amounts, in the mixture fed to the crystallizer in order to improve the crystallization of the 2,6-dimethylnaphthalene. The amount of lights included in the mixture fed to the crystallizer apparatus is an amount that provides for the efficient crystallization of 2,6-dimethylnaphthalene, suitably at least about 5 weight percent of the total mixture crystallized, preferably at least about 7 weight percent, and most preferably at least about 10 weight percent of the total mixture subjected to crystallization. Preferably no more than about 25 weight percent of the mixture subjected to crystallization is lights.

In addition to the amount of lights present in the mixture crystallized, the relative amounts of the other components in the mixture affects the crystallization of the 2,6-dimethylnaphthalene. As stated hereinabove, the weight ratio of high melting components, HM, to low melting components, LM, must be:

$$\frac{HM}{LM} < 0.03(T - 50) + A,$$

wherein the high melting components have melting points above about 70° F. and can include, for example, 2,6-dimethylnaphthalene, 1,5-dimethylnaphthalene, 2,7-dimethylnaphthalene and 2-methylnaphthalene (2-MN). The low melting components include, for example, 1,6-dimethylnaphthalene, 1,7-dimethylnaphthalene, 1-methynaphthalene and other light boiling components, the trimethylnaphthalene fraction and the heavy boiling components. The value of A is no greater than 1.0, more preferably no greater than 0.9. Most preferably, A is about 1.0 to 0.9. Thus, we have found that a mixture containing the composition X shown below could not be crystallized in a scraped-wall crystallizer to isolate 2,6-dimethylnaphthalene at a crystallization temperature of 70° F. whereas, the composition Y shown below was successfully crystallized at 85° F. to yield 2,6-dimethylnaphthalene in high yield and purity using a scraped-wall crystallizer apparatus to conduct the crystallization. As shown below, the feed X has a HM/LM ratio of 1.6 and at a crystallization temperature of 70° F., equation (5) is not satisfied where A is 1.0. Composition Y, however, has a HM/LM value of 1.2 and at a crystallization temperature 85° F., equation (5) is satisfied where A is 1.0.

| COMPONENT | CRYSTALLIZER FEED COMPOSITION (WT. %) | | |
| --- | --- | --- | --- |
| | X | Y | Z |
| Lights[a] | 4.0 | 0.7 | 7.2 |
| 2-MN | 0.9 | 0.6 | 3.1 |
| 1-MN | 0.3 | 0.5 | 1.1 |
| 1,5-DMN | 9.2 | 13.3 | 7.5 |
| 1,6-DMN | 33.0 | 41.4 | 27.6 |
| 2,6-DMN | 41.4 | 39.0 | 43.5 |
| 1,7-DMN | 0.8 | 1.8 | 1.4 |
| 2,7-DMN | 9.3 | 2.4 | 6.1 |
| Heavies | 1.1 | 0.4 | 2.5 |
| Cryst. Temp. ° F. | 70 | 85 | 70 |
| HM/LM | 1.6 | 1.2 | 1.5 |
| 0.03 (T-50) + 1.0 | 1.6 | 2.0 | 1.6 |
| HM/LM < 0.03 (T-50) + 1.0 | No | Yes | Yes |
| 2,6-DMN (Yield, %/Purity, %) | inoperable | 75.6/99 | 77.8/97.5 |

[a]Other than 1-MN

Thus, it is not only the quantity of the light boiling components in the mixture that provides for efficient crystallization, but the weight ratio of high melting components to low melting components and the crystallization temperature. At times, the ability to adjust the ratio of high melting components to low melting components is not feasible unless the adjustment is made by altering the level of light boiling components, i.e., a type of low melting component, in the feed mixture to the crystallizer. For example, mixture Z in the table above, which mixture contained more lights than mixture X, was effectively crystallized in a scraped-wall crystallizer apparatus providing 2,6-dimethylnaphthalene in good purity and high yield. Using the lights to assist in the crystallization of 2,6-dimethylnaphthalene is advantageous because it does not introduce extraneous components into the process stream, which would occur if a solvent were used. After crystallization, and after the desired crystalline 2,6-dimethylnaphthalene is separated from the mother liquor, the mother liquor, which contains the light and heavy components, can be fractionated into its various components. One or more of such fractions can be recycled to the isomerization or crystallization step if desired, or one or more can be purged from the process and used, for example, as fuel.

In addition to using lights to adjust the HM/LM ratio, the 1,5-dimethyltetralin (1,5-DMT) produced in the second step of the alkenylation process can also be used. This component, which has a melting point of less than 70° F., is also highly suitable because it does not add extraneous materials to the process. When used, the amount of 1,5-DMT in the mixture crystallized is suitably at least about 2 wt. % of the mixture crystallized, preferably at least about 5 wt. % and more preferably at least about 7 wt. %.

The lights (i.e., light, low boiling components) useful in the method of this invention comprise a complex mixture of compounds and where such mixture is produced during the manufacture or isolation of 2,6-dimethylnaphthalene. Preferably, the lights comprise a mixture of organic compounds which mixture has a boiling point lower than the boiling point of 2- methylnaphthalene, and more preferably where they are obtained by fractionating the mixture produced in the alkenylation process subsequent to the isomerization step where 1,5-dimethylnaphthalene is isomerized to 2,6-dimethynaphthalene. The lights mixture has a melting point below 70° F., and thus is a low-melting component. These lights typically contain o-xylene, 1-methyl-2-pentylbenzene, 5-orthotolylpentene-1, 5-orthotolyl-pentene-2, 1,5-dimethyltetralin, 1,6-dimethyltetralin, other dimethyltetralin isomers, and 1-methylnaphthalene.

As described hereinabove, the method of this invention is also useful for isolating, by crystallization, 2,6-dimethylnaphthalene from other sources or produced by other synthetic routes. For example, the method of this invention can be used to crystallize 2,6-dimethylnaphthalene isolated from fractions obtained from the catalytic or thermal cracking of petroleum, such as the dimethylnaphthalene portion separated by distillation from recycle oil in the FCC process. The method of this invention can also be used to isolate 2,6-dimethylnaphthalene from dimethylnaphthalene-containing fractions obtained from coal tar. The method of this invention can also be used to isolate, by crystallization, 2,6 -dimethylnaphthalene produced via the method disclosed in U.S. Pat. Nos. 5,008,479; 5,023,390; and 5,068,480.

The crystallization apparatus most suitable for crystallizing 2,6-dimethylnaphthalene according to the method of this invention is a scraped-wall type crystallizer. In these types of crystallization apparatus spring-loaded scraper blades, typically manufactured from a flexible, polymeric material having resistance to high temperatures, resistance to chemical attack, and good wear resistance and lubricity (for example, nylon, Teflon®, Torlon®, such as Torlon® 4301 or 4302, or Hydlar®), rotates within a crystallization drum while the polymeric scraper blades "scrape" the inside wall of the crystallization drum. The outside of the crystallization drum is equipped with cooling jackets to cool the liquid being crystallized to the desired crystallization temperature while the blades in the scraped-wall crystallizer scrape along the inside cylindered walls of the crystallization drum. The scraped-wall crystallizer suitably contains a separate pumping device to maintain the contents of the crystallization drum well mixed. Suitable scraped-wall crystallizers are available from Victoria Machine Works, Victoria, Tex. Two or more scraped-wall crystallizers can be used in series, each operating at successively decreasing temperatures, and where the feed to the second comprises a slurry produced in the first crystallizer. A double-pipe scraped-wall crystallizer can also be used along with the drum-type scraped-wall crystallizer. While scraped-wall crystallizers are preferred for the method of this invention, other crystallization apparatus can be used, for example, a draft tube crystallizer. However, with these other crystallizers, a lower HM/LM ratio will likely be necessary, i.e., where A is no more more than about 0.6. The crystallization method disclosed herein can be conducted in a batch or continuous manner.

DETAILED DESCRIPTION OF THE FIGURES

Figure 1:
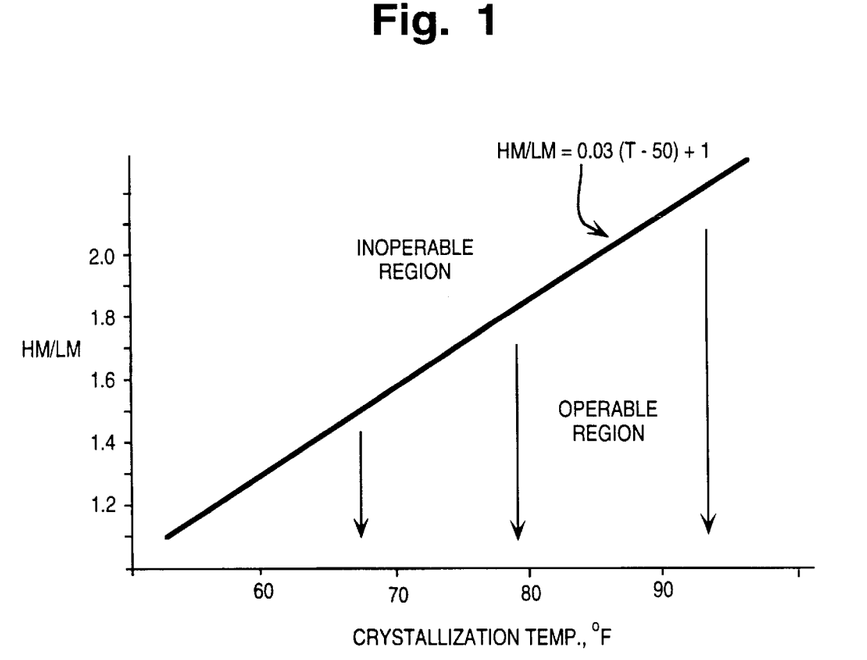
FIG. 1 shows in graphical form preferred parameters for operating the method of this invention.

FIG. 1 is a graph showing the operating range for the method of this invention. The region below the line termed "operable," identifies the various crystallization temperatures and ratios of HM/LM that can be used at such temperatures to provide for the efficient crystallization of 2,6-dimethylnaphthalene in a scraped-wall crystallizer. In FIG. 1, the line establishing the operable region corresponds to the equation:

$$\frac{HM}{LM} = 0.03 \, (T - 50) + 1.0.$$

Figure 2:
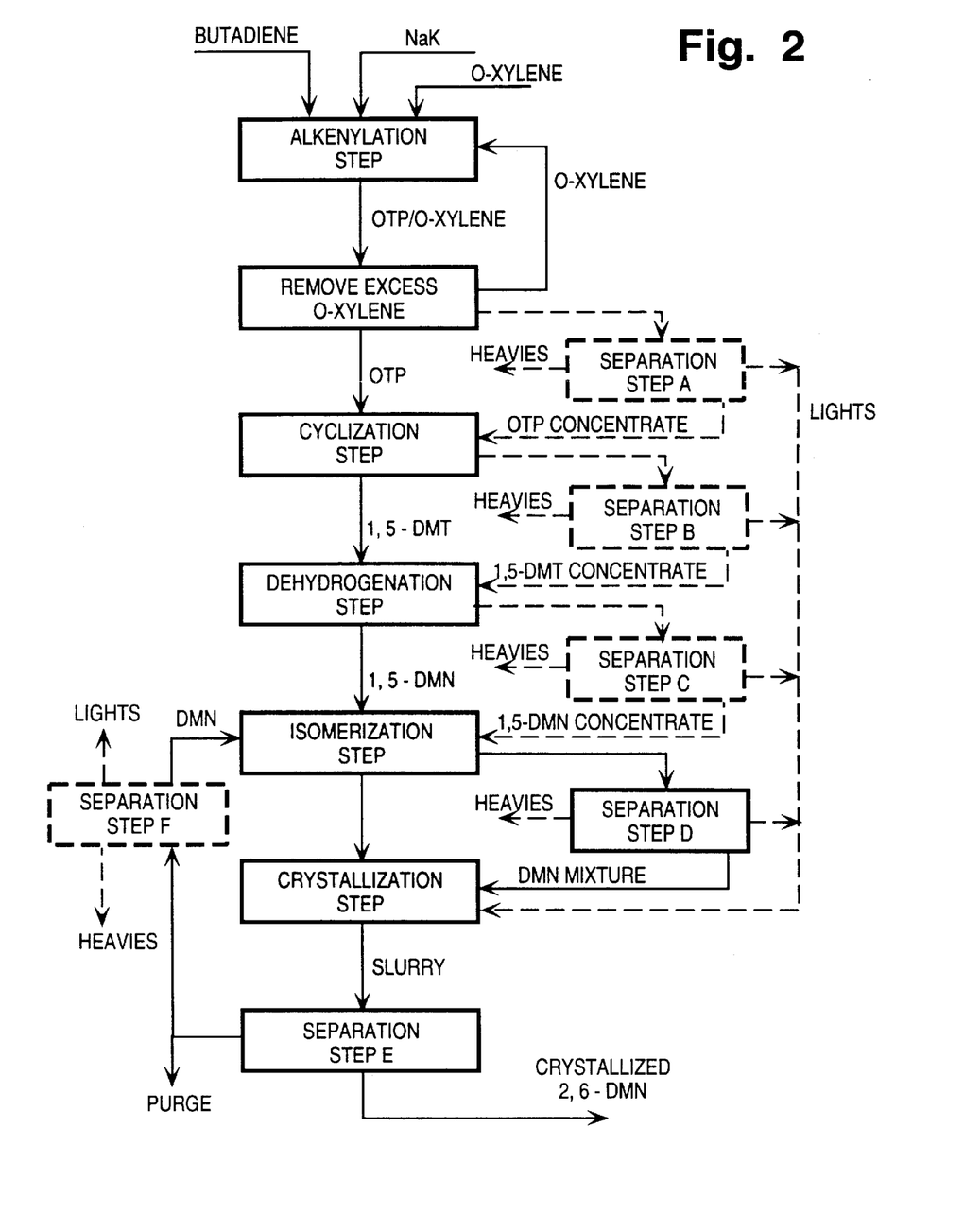
FIG. 2 is a flow diagram showing a preferred embodiment for operating the method of this invention.

FIG. 2 is a flow diagram representing a preferred embodiment for operating the method of this invention. In FIG. 2, the dotted lines represent optional process steps that can be operated individually or in any combination. In this preferred embodiment, butadiene and o-xylene are reacted in a liquid phase reaction using a molar excess of o-xylene relative to butadiene and catalyzed by a metallic sodium-potassium (NaK) catalyst. In the next process step, the excess o-xylene is removed, typically by distillation, and is recycled to the alkenylation reaction mixture. The ortho-tolylpentene (OTP) separated from the o-xylene is either sent directly to the cyclization reactor in the Cyclization Step or subjected to a Separation Step A, typically distillation, to remove components having a boiling point lower and/or higher than about the boiling point the OTP, thereby forming an OTP concentrate. The OTP is subsequently cyclized to 1,5-dimethyltetralin (1,5-DMT) in the Cyclization Step using a suitable cyclization catalyst, and where the cyclization can be conducted in either liquid or gas phase mode. The 1,5-DMT produced from the Cyclization Step is either sent directly to the Dehydrogenation Step or first subjected to a Separation Step B, typically distillation, where components having a boiling point lower and/or higher than about the boiling point of 1,5-DMT are removed. In the Dehydrogenation Step, the 1,5-DMT is dehydrogenated to 1,5-dimethylnaphthalene (1,5-DMN) in either a liquid phase or gas phase reaction using a suitable dehydrogenation catalyst. The product mixture from the Dehydrogenation Step is sent directly to the Isomerization Step or subjected to a Separation Step C, typically distillation, where the materials having a boiling point lower and/or higher than about the boiling point of 1,5-dimethylnaphthalene are removed. The product 1,5-dimethylnaphthalene from the Dehydrogenation Step is isomerized in the Isomerization Step in either a gas or liquid phase reaction using a suitable isomerization catalyst to form a mixture of dimethylnaphthalenes, including the desired 2,6-dimethylnaphthalene. The mixture produced by the Isomerization Step is directed to a Separation Step D, typically distillation, where a portion of the lights and at least a portion of the heavies can be removed. The resulting molten mixture containing DMN isomers is directed to the Crystallization Step where the mixture is cooled to crystallize the desired 2,6-dimethylnaphthalene in a crystallization apparatus. After the crystallization, which is preferably conducted in a scraped-wall crystallizer or two or more scraped-wall crystallizers in series, at a temperature in the range of about 50 to about 150° F., more preferably 60 to 140° F., the crystalline 2,6-dimethylnaphthalene is separated from the crystallization mother liquor in Separation Step E using a solid-liquid separation device such a centrifuge, filter, settling tank, etc. The recovered 2,6-dimethylnaphthalene can be subjected to additional purification procedures, if desired, such as washing, crystallization from a melt of the product at a temperature higher than the temperature used in the Crystallization Step, recrystallization from a solvent such as a low molecular weight carboxylic acid such as acetic acid, a low molecular weight alcohol including methanol, ethanol, isopropanol and the like, or a low boiling hydrocarbon such as hexane, octane, nonane, a mixture of low boiling hydrocarbons, or a combination of such purification procedures. The mother liquor recovered from the crystallization of the 2,6-dimethylnaphthalene contains lights, 2-methylnaphthalene, a mixture of dimethylnaphthalenes including 2,6-dimethylnaphthalene that was not crystallized, a mixture of trimethylnaphthalenes, and various heavy components that have boiling points higher than about the boiling points of the trimethylnaphthalenes. The mother liquor can be separated in Separation Step F, preferably by fractional distillation, into lights, the dimethylnaphthalenes and the heavies. The lights can be recycled to the Crystallization Step. The dimethylnaphthalenes isomer fraction, as shown in FIG. 2, is preferably recycled to the Isomerization Step. Some of the dimethylnaphthalene fraction may also eliminated after Separation Step E in order to prevent a build-up of 2,7-dimethylnaphthalene. Some or all of the heavies are removed from the overall process and are disposed as fuel or sold as by-product.

In the method of this invention, the composition of the mixture in the Crystallization Step in FIG. 2, is such that the equation, $$\frac{HM}{LM} < 0.03\,(T-50) + A$$

is satisfied, where HM, LM and T are described hereinabove, and A is no greater than 1.0. In the method of this invention, the HM/LM ratio is efficiently adjusted by adjusting the content of the lights in the mixture sent to the Crystallization Step. The adjustment in the amount of lights is preferably made during the Separation Step D shown in the FIG. 2 where the product from the Isomerization Step is subjected to a separation procedure, preferably one or more fractionations, where lights and heavies are removed from the product formed during the Isomerization Step. In this fractionation step, the amount of lights and heavies included in the material sent to the Crystallization Step can be adjusted to meet the requirements of equation (5). Lights from each of Separation Steps A–C can optionally be added to the Crystallization Step in order to have the composition that is crystallized conform to equation (5) hereinabove. Although not depicted in FIG. 2, 1,5-DMT product produced in the Cyclization Step can be added to the mixture crystallized in the Crystallization Step. As discussed hereinabove, 1,5-DMT is a low melting component and can be used to adjust the HM/LM ratio so that it meets the requirements of equation (5).

The following examples will serve to further illustrate the method of this invention; however, they are not intended to limit the scope thereof.

Feed mixtures corresponding to that shown in the following Tables 1 and 2 were crystallized at the temperatures indicated in the tables using a scraped-wall crystallization apparatus as described hereinabove. The crystallizer had a volume of 5 gal. and the scraper had Teflon® blades scraping the crystallizer wall. The feed mixtures used for the crystallization runs reported in the tables were prepared by the alkenylation process. As shown, the feed mixtures contained various amounts of lights or 1,5-dimethyltetralin as some of the low melting components. The feed materials were processed through the scraped-wall crystallizer in a continuous manner. Samples were analyzed by gas chromatography to determine their composition. Also, the scraped-walled crystallizer used for these experiments was equipped with a viewing port to allow for the observation of the internals of the crystallizer to see if there was an unusual or excessive build-up of rime. Each crystallization run lasted approximately 16 hours.

As the results in Tables 1 and 2 show, when the HM/LM ratio for the crystallization feed at crystallization temperature T was less than the value (0.03 (T-50)+A), the crystallization was successful in the scraped-wall crystallizer producing 2,6-dimethylnaphthalene in high yield and purity. However, when the value of HM/LM was not less than (0.03 (T-50)+A), the crystallizer was inoperative.

TABLE 1

| Feed Components (wt. %) | Crystallization Run # | | | | | |
|---|---|---|---|---|---|---|
| | 1 | 2 | 3 | 4 | 5 | 6 |
| "Lights"[a] | 24.0 | 24.0 | 35.3 | 7.2 | 0.7 | 4.0 |
| 2-MN | 8.2 | 8.2 | 12.1 | 3.1 | 0.6 | 0.9 |
| 1-MN | 2.2 | 2.2 | 3.2 | 1.1 | 0.5 | 0.3 |
| 1,5-DMN | 2.1 | 2.1 | 1.6 | 7.5 | 13.3 | 9.2 |
| 1,6-DMN | 6.5 | 6.5 | 5.0 | 27.6 | 41.2 | 33.0 |

TABLE 1-continued

| Feed Components (wt. %) | Crystallization Run # | | | | | |
|---|---|---|---|---|---|---|
| | 1 | 2 | 3 | 4 | 5 | 6 |
| 2,6-DMN | 55.7 | 55.7 | 41.8 | 43.5 | 39.0 | 41.4 |
| 1,7-DMN | 0.5 | 0.5 | 0.2 | 1.4 | 1.8 | 0.8 |
| 2,7-DMN | 0.7 | 0.7 | 0.6 | 6.1 | 2.4 | 9.3 |
| Heavies | 0.1 | 0.1 | 0.1 | 2.5 | 0.4 | 1.0 |
| CONDITIONS | | | | | | |
| HM/LM[b] | 2.0 | 2.0 | 1.3 | 1.5 | 1.2 | 1.6 |
| Crystallization Temp., °F. | 85 | 70 | 70 | 70 | 85 | 70 |
| 0.03 (T-50) + 1.0 | 2.1 | 1.6 | 1.6 | 1.6 | 2.1 | 1.6 |
| RECOVERY OF 2,6-DMN FROM CRYSTALLIZATION | | | | | | |
| Yield of 2,6-DMN, wt. % | 77.0 | Inoperable | 66.7 | 77.8 | 75.6 | Inoperable |
| Purity of 2,6-DMN, wt. % | 97.9 | NA | 97.7 | 97.5 | 99.0 | NA |

[a]Lights other than 1-MN produced during the preparation of 2,6-dimethylnaphthalene by the alkenylation process. Lights have a boiling point below about 470° F., at atmospheric distillation pressure.
[b]Weight ratio of high melting (HM) components, i.e., 1,5-DMN, 2,6-DMN, 2,7-DMN and 2-MN, in feed mixture to low melting (LM) components, i.e., 1,6-DMN, 1,7-DMN, 1-MN and other lights, and heavies.

TABLE 2

| Feed Components (wt. %) | Crystallization Run # | | | |
|---|---|---|---|---|
| | 7 | 8 | 9 | 10 |
| 1,5-DMT | 38.8 | 45.2 | 45.2 | 4.7 |
| "Lights"[a] | 4.1 | 4.5 | 4.5 | 4.6 |
| 2-MN | 0.2 | 0.2 | 0.2 | 2.0 |
| 1-MN | 0.1 | 0.1 | 0.1 | 0.9 |
| 1,5-DMN | 2.5 | 2.4 | 2.4 | 7.6 |
| 1,6-DMN | 5.5 | 4.8 | 4.8 | 27.3 |
| 2,6-DMN | 47.7 | 41.8 | 41.8 | 43.0 |
| 1,7-DMN | 0.3 | 0.3 | 0.3 | 1.2 |
| 2,7-DMN | 0.6 | 0.5 | 0.5 | 6.2 |
| Heavies | 0.1 | 0.4 | 0.4 | 2.6 |
| CONDITIONS | | | | |
| HM/LM[b] | 1.0 | 0.8 | 0.8 | 1.4 |
| Crystallization Temp., °F. | 70 | 70 | 50 | 70 |
| 0.03 (T-50) + 1.0 | 1.6 | 1.6 | 1.0 | 1.6 |
| RECOVERY OF 2,6-DMN FROM CRYSTALLIZATION | | | | |
| Yield of 2,6-DMN, wt. % | 67.8 | 67.5 | 71.0 | 76.6 |
| Purity of 2,6-DMN, wt. % | 99.9 | 99.9 | 99.9 | 95.4 |

[a]Lights other than 1-MN and 1,5-DMT produced during the preparation of 2,6-dimethylnaphthalene by the alkenylation process. Lights have a boiling point below about 470° F., at atmospheric distillation pressure.
[b]Weight ratio of high melting (HM) components, i.e., 1,5-DMN, 2,6-DMN, 2,7-DMN, and 2-MN in feed mixture to low melting (LM) components, i.e., 1,6-DMN, 1,7-DMN, 1-MN and 1,5-DMT and other lights, and heavies.

While only certain embodiments have been set forth, alternative embodiments and various modifications will be apparent from the above description to those skilled in the art. These and other alternatives are considered equivalents and within the spirit and scope of the present invention.

That which is claimed is:

1. A method for crystallizing 2,6-dimethylnaphthalene comprising maintaining, at a temperature sufficient to cause the crystallization of 2,6-dimethylnaphthalene, a mixture consisting essentially of lights, heavies, monomethylnaphthalenes, and dimethyl naphthalenes, said lights comprising between at least about 5 weight percent and less than about 25 weight percent of the mixture and being produced during the preparation or isolation of 2,6-dimethylnaphthalene, said lights further having a boiling point lower than about 500° F., and said heavies being produced during the preparation or isolation of 2,6-dimethylnaphthalene and having a boiling point greater than about 520° F.

2. The method of claim 1 wherein the mixture is prepared by an alkenylation process comprising, alkenylating o-xylene with 1,3-butadiene in the presence of an alkali metal to form orthotolylpentene, cyclizing orthotolylpentene to form 1,5-dimethyltetralin, dehydrogenating the dimethyltetralin to form a mixture comprising 1,5-dimethylnaphthalene, and isomerizing the 1,5-dimethylnaphthalene to form the mixture comprising 2,6-dimethylnaphthalene.

3. The method of claim 2 wherein the mixture comprises at least about 7 weight percent lights.

4. The method of claim 2 wherein the temperature is about 50° F. to about 150° F.

5. The method claim 4 wherein the mixture contains at least about 20 weight percent 2,6-dimethylnaphthalene.

6. The method of claim 2 wherein the lights include lights formed during the alkenylating, cyclizing, dehydrogenating and isomerizing steps.

7. The method of claim 1 wherein the lights have a boiling point of less than about the boiling point of 2-methylnaphthalene.

8. The method of claim 1 practiced in a batch manner.

9. The method of claim 1 practiced in a continuous manner.

* * * * *

UNITED STATES PATENT AND TRADEMARK OFFICE
CERTIFICATE OF CORRECTION

Page 1 of 2

PATENT NO. : 5,977,426
DATED : November 2, 1999
INVENTOR(S) : Thomas G. Smith, et. al.

It is certified that error appears in the above-identified patent and that said Letters Patent is hereby corrected as shown below:

| Col. | Line | | |
|------|------|--|--|
| 8 | 55 | "2,6-dimethynaphthalene." should read: "2,6-dimethylnaphthalene." | |
| 9 | 44 | " "operable," " should read: " "operable", " | |
| 10 | 37 | "such a centrifuge," should read: "such as a centrifuge," | |
| 10 | 61,62 | "may also eliminated" should read: "may also be eliminated" | |

UNITED STATES PATENT AND TRADEMARK OFFICE
CERTIFICATE OF CORRECTION

PATENT NO. : 5,977,426
DATED : November 2, 1999
INVENTOR(S) : Thomas G. Smith, et. al.

It is certified that error appears in the above-identified patent and that said Letters Patent is hereby corrected as shown below:

| Col. | Line | |
|---|---|---|
| 2 | 37 | " —— H $\xrightarrow{\text{Dehydrogenation Catalyst}}$ " should read: "-H$_2$ $\xrightarrow{\text{Dehydrogentation Catalyst}}$ " |
| 7 | 45 | "X has a" should read: "X has an" |
| 7 | 49 | "temperature 85°F," should read: "temperature of 85°F," |

Signed and Sealed this

First Day of May, 2001

Attest:

NICHOLAS P. GODICI

*Attesting Officer*  *Acting Director of the United States Patent and Trademark Office*